(12) United States Patent
Garrison, Jr.

(10) Patent No.: US 6,194,209 B1
(45) Date of Patent: Feb. 27, 2001

(54) SYSTEMS AND METHODS FOR STANDARDIZING HERBAL EXTRACTS UTILIZING ABSORPTION STUDIES

(75) Inventor: Robert H. Garrison, Jr., Carlsbad, CA (US)

(73) Assignee: Next Pharmaceuticals, Inc., Irvine, CA (US)

( * ) Notice: Subject to any disclaimer, the term of this patent is extended or adjusted under 35 U.S.C. 154(b) by 0 days.

(21) Appl. No.: 09/257,329

(22) Filed: Feb. 25, 1999

(51) Int. Cl.[7] ........................................................ C12N 5/00
(52) U.S. Cl. .......................... 435/395; 422/68.1; 422/69; 422/102; 422/942; 435/1.1; 435/1.2; 435/4; 435/325; 436/8; 436/34; 436/514
(58) Field of Search .................................. 435/4, 325, 1.1, 435/1.2, 395; 422/68.1, 69, 102, 942; 436/8, 34, 514

(56) References Cited

U.S. PATENT DOCUMENTS

| | | |
|---|---|---|
| 4,994,442 * | 2/1991 | Gil et al. . |
| 5,308,764 * | 5/1994 | Goodwin et al. . |
| 5,637,563 | 6/1997 | Khwaja . |
| 5,780,037 | 7/1998 | Khwaja . |
| 6,040,188 * | 3/2000 | Holman . |

* cited by examiner

*Primary Examiner*—Leon B. Lankford, Jr.
(74) *Attorney, Agent, or Firm*—Stetina Brunda Garred & Brucker

(57) ABSTRACT

Systems and methods for deriving standardized formulations and extracts of herbal remedies, plant extracts, and the like, based upon the rate of absorption and plasma concentration levels attained thereby, when such compositions are administered orally. According to a preferred embodiment, the system comprises a harvested section of small intestine from a mammal and interposed between a first solution having a known quantity of the pharmaceutical composition suspended or dissolved therewithin and a second solution comprising liquid plasma or a buffer solution. The section of intestinal tissue is oriented such that the mucosal layer is oriented toward the first solution whereas the muscularis is oriented toward the second solution. The second solution is periodically analyzed, both qualitatively and quantitatively, to determine the presence and concentration of one or more markers, and in particular any sub-component or metabolites thereof, that has diffused across the intestinal tissue. The identification of such markers may be utilized in the extraction or manufacturing process to enable standardized extracts to be derived.

28 Claims, 1 Drawing Sheet

SYSTEMS AND METHODS FOR STANDARDIZING HERBAL EXTRACTS UTILIZING ABSORPTION STUDIES

CROSS-REFERENCE TO RELATED APPLICATIONS

Not Applicable.

STATEMENT RE: FEDERALLY SPONSORED RESEARCH/DEVELOPMENT

Not Applicable.

BACKGROUND OF THE INVENTION

As is well-known in the pharmaceutical industry, in order to establish the safety and efficacy of a drug, as well as the most therapeutic dosage thereof, it is necessary to establish the specific pharmacokinetics and metabolism associated with such drug when the same is administered to a patient via clinical pharmacology. In this respect, due to the tendencies of different compounds to be absorbed at varying rates, achieve varying peak serum concentrations, and become metabolized and excreted via one or more metabolic pathways, proper formulation is crucial to insure that an administered dosage of a given pharmaceutical composition is neither excessive, so as to cause possible adverse side effects or toxicity, nor below certain threshold concentrations, such that the composition fails to produce the desired therapeutic benefit.

To establish such parameters, detailed and exhaustive in vivo (in animals) and in vitro studies are conducted to obtain data on pharmaceutical safety and efficacy in order to demonstrate that there will be no unreasonable hazard in initiating trials in human beings. The rate and extent of absorption and excretion of a given compound are usually determined during the course of the subacute toxicity studies by following changes in plasma concentration of the pharmaceutical composition after oral and parenteral administration. Additionally, organs and tissues may have to be analyzed directly for their content of the pharmaceutical composition, as well as any sub-components or metabolites thereof.

To the extent toxicity and efficacy can be sufficiently evaluated, further tests are necessary to determine preferred formulations of the commercial pharmaceutical composition product to be used in treating patients. These formulation considerations are particularly sensitive where pharmaceutical manufacturers strive to produce formulations of pharmaceutical compositions that may be administered in daily doses. In this respect, it is known that pharmaceutical compositions administered daily achieve the highest degree of patient compliance and acceptance, as opposed to pharmaceutical formulations requiring administration two or more times a day or every other day. As is well-known, however, to provide for such precise dosing requires meticulous analysis and formulation such that a particular dosage coincides with a sufficient degree of absorption, distribution and bioavailability within a sufficiently large cross-section of the population so as to produce the desired therapeutic benefit.

While protocols have been established for evaluating the clinical pharmacology of so-called "ethical" pharmaceutical compositions, such standards currently do not apply for herbal remedies or plant extracts that, although not supported by clinical data, are believed to produce significant therapeutic benefits for a variety of conditions. As a consequence, no established standards for clinical testing procedures currently exist, let alone the formulations or dosages of a given composition that are believed to be universally accepted as the preferred dosage ranges. In this regard, most herbal remedy compositions sold in this country merely use powdered whole herb or occasionally standardized extracts obtained from companies that may or may not have completed clinical trials on the extracts, or sell the extracts as prescription drugs in one or more foreign countries. In cases where such standardized extracts are not available, manufacturers tend to obtain extracts from high-quality suppliers and rely solely upon the quality control measures implemented thereby to insure uniform concentrations of such active ingredients.

Such manufacturing procedures, however, are ill-suited in pharmaceutical composition manufacturing practices insofar as such practices tend to be unreliable, which consequently results in the production of pharmaceutical compositions that contain too much or not enough of the active ingredient necessary to bring about the therapeutic benefit. Moreover, even to the extent the active ingredient in a given herbal remedy or plant extract is present in an optimal concentration necessary to produce a given therapeutic benefit, how such active ingredient is ultimately formulated with other ingredients, such as an excipient that slows the absorption of such active ingredient, or how such active ingredient reacts to a manufacturing process, such as mixing which potentially destroys the biologically active form of the active ingredient, yet further thwarts the ability of such formulations to uniformly and consistently impart the desired therapeutic benefit.

These threats extend across all lines of pharmaceutical manufacturing practices, whether it be in making tablets, lozenges, liquid suspensions or gel-suspension caplets. Moreover, such threats are compounded further to the extent the active ingredient of such herbal remedy or plant extract comprises a multi-component botanical, the extracts of which are collectively believed to produce a desired therapeutic benefit. However, substantial difficulty occurs when trying to formulate, let alone standardize, herbal extracts that possess the necessary active ingredients, as well as their respective concentrations.

Accordingly, there is a need in the art for a system and method by which pharmaceutical compositions, and in particular herbal remedies and plant extracts, can be evaluated for absorption properties for use in deriving standardized formulations and/or extracts thereof. There is additionally a need in the art for a method for determining the absorption properties of herbal remedies and plant extracts that can reliably reproduce the rate by which the same are absorbed into the human body and the resultant serum concentrations achieved thereby, particularly when the same are administered orally, to thus enable such extract formulations to be standardized. There is yet a further need in the art for a method for determining the absorption rates of herbal remedies and plant extracts that is simple to construct, utilizes relatively inexpensive materials, and is based upon accepted principles and parameters for establishing drug absorption activity using biological absorption models.

BRIEF SUMMARY OF THE INVENTION

The present invention specifically addresses and alleviates the above-identified deficiencies in the art. In this regard, the present invention is directed to systems and methods for deriving standardized formulations and/or extracts of pharmaceutical compositions, and in particular herbal remedies, plant extracts, and the like, by determining the rate of absorption of such compositions through tissues of the gastrointestinal tract as would occur when such compositions are ingested orally. Such systems and methods are particularly effective in determining the peak serum concentrations of such compositions, as well as any sub-components or metabolites thereof, that a given dosage of the pharmaceutical composition would achieve when administered orally to thus facilitate the derivation of standard formulations for such pharmaceutical composition products.

According to a preferred embodiment, the system comprises a section of the tissue harvested from the gastrointestinal tract of a suitable mammalian model, such as rats, rabbits and the like, that is interposed between a first solution comprising an aqueous buffer having a known concentration of the pharmaceutical composition suspended or dissolved therein, and a second solution of liquid plasma or other type of buffer having blood serum protein suspended therein or otherwise simulate human blood systems. The section of tissue preferably comprises a section harvested from the small intestine due to the fact that the small intestine is the site where most absorption activity occurs. The section of tissue is interposed between the first and second solutions such that the mucosa of the tissue is oriented toward the first solution containing the known concentration of pharmaceutical composition and the muscularis of the tissue facing the second solution of plasma.

Once the first and second solutions have sufficiently immersed the opposed sides of the tissue, the second solution is periodically analyzed, using conventional qualitative and quantitative chemical analysis, to determine the rate by which the pharmaceutical composition, as well as any metabolites or components thereof, permeate and diffuse through the intestinal tissue and eventually dissolve within the second solution or otherwise become bound to the protein suspended therein, which is thus indicative of serum concentration levels that would be attained in the mammalian subject.

From such data, there may be derived standardized formulations for such herbal/botanical extracts to thus enable the same to be manufactured such that the same contain the appropriate concentrations thereof to produce the desired therapeutic benefit. It is further believed that such absorption rates can be particularly effective in standardizing herbal extracts wherein the extracts are believed to contain a multiplicity of components or sub-components that must necessarily be present at specified concentrations to thus enable the same to collectively produce a desired therapeutic benefit.

In further refinements of the invention, it is contemplated that in applications where it is desired to determine the rate of absorption through the small intestine, the pharmaceutical composition sought to be analyzed for absorption rate may first be subjected to gastric juice and stomach enzymes to more closely mimic the conditions the composition would typically encounter prior to being introduced into the small intestine where the same would ultimately be absorbed. It is additional contemplated that additional systems may be designed to determine absorption rates through different tissues of the gastrointestinal tract, including the stomach wall, duodenal wall, colonic wall, as well as specific portions of the small intestine including the ileal wall and jejunal wall. It is also contemplated that systems utilizing cell lines such as $CaCO_2$ that simulate human intestinal absorption may be designed.

It is therefore an object of the present invention to provide a system and method for deriving standardized formulations of herbal remedies, plant extracts, and the like, and in particular any active ingredient(s) or sub-component(s) thereof, based upon the rate of absorption of the components of such herbal remedy and/or plant extract from the gastrointestinal tract to the bloodstream.

Another object of the present invention to provide a system and method for determining the rate of absorption of a pharmaceutical composition, and in particular an herbal remedy, plant extract, and the like, as well as any active ingredient or sub-component thereof, from the gastrointestinal tract to the bloodstream.

Another object of the present invention is to provide a system and method for determining the pharmacokinetics, and in particular the absorption rates of a pharmaceutical composition, including herbal remedies, plant extracts, and the like, that are effective in accurately determining the plasma concentration levels of the composition and/or any sub-component or metabolite thereof that would be attained when a given amount of such pharmaceutical composition is ingested by a mammalian subject including, but not limited to, human beings.

Another object of the present invention is to provide a system and method for determining the rate of absorption of a pharmaceutical composition, and in particular an herbal remedy, plant extract, and the like, for deriving standardized formulations and/or extracts thereof that utilize reliable and reproducible biological models.

Still further objects of the present invention are to provide systems and methods for determining the rate of absorption of a pharmaceutical composition, and in particular an herbal remedy, plant extract, and the like, for deriving standardized formulations and/or extracts thereof that are simple to deploy, biologically sound, closely mimic in vivo conditions, are relatively inexpensive and have widespread applicability over virtually every type of pharmaceutical compound ingested via the gastrointestinal tract for use in determining the specific pharmacokinetics associated therewith.

BRIEF DESCRIPTION OF THE SEVERAL VIEWS OF THE DRAWING

These, as well as other features of the present invention will become more apparent upon reference to the drawings wherein.

DETAILED DESCRIPTION OF THE INVENTION

Figure 1:
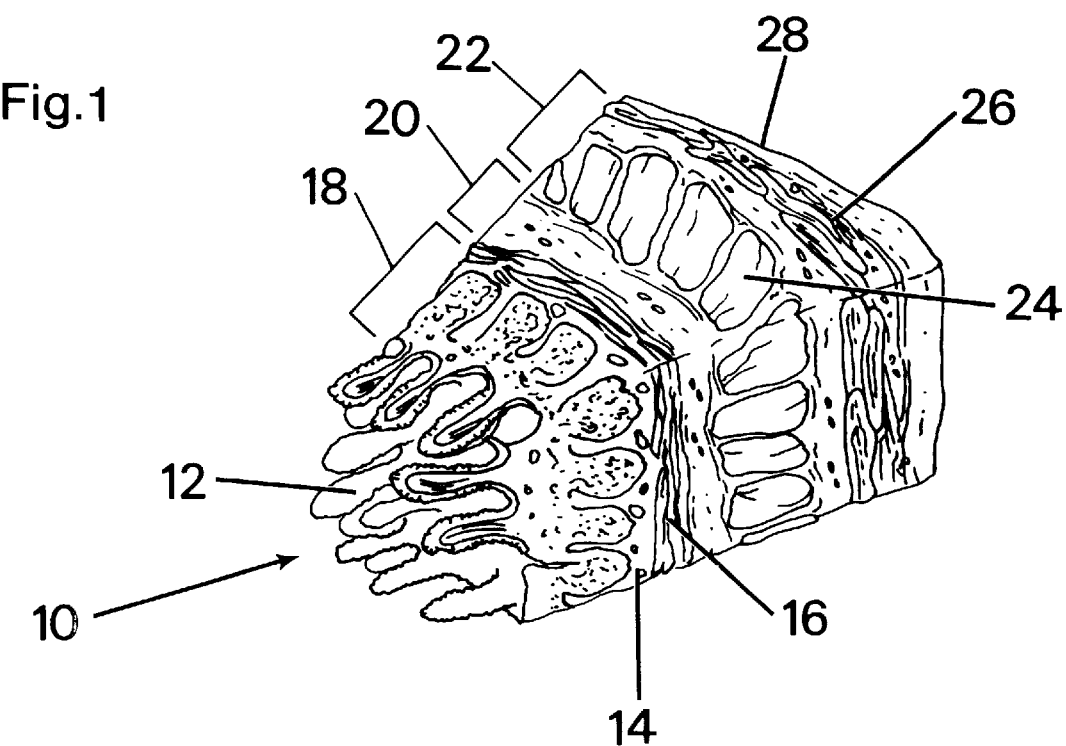
FIG. 1 is a perspective view of a section of ileal wall of the small intestine, as harvested from a mammal.

The detailed description as set forth below in connection with the appended drawings is intended as a description of the presently preferred embodiments of the invention, and is not intended to represent the only form in which the present invention may be constructed or utilized. The description sets forth the functions and sequences of steps for constructing and operating the invention in connection with the illustrated embodiments. It is understood, however, that the same or equivalent functions and sequences may be accomplished by different embodiments and that they are also intended to be encompassed within the scope of this invention.

Referring now to the drawings, there is shown a cross-section of tissue 10 harvested from the small intestine of mammal and a system 30 constructed in accordance to a preferred embodiment of the present invention by which such section of tissue 10 may be utilized to determine the rate by which a pharmaceutical composition, or any sub-components or metabolites thereof, become systemically absorbed when a known quantity of such pharmaceutical composition is ingested, as would occur when such composition is administered orally. As used herein, it will be understood that the term "pharmaceutical composition" may include any type of compound, composition or chemical entity, as well as any sub-component or metabolite thereof, that is ingested for the purpose of bringing about a specific therapeutic benefit. The term "pharmaceutical composition" will further expressly include any and all types of herbal remedies, plant extracts, and the like, that are currently exempt from multi-phase clinical testing as required by the Food & Drug Administration for new drugs, as well as multi-component remedies and extracts that utilize a plurality of compositions to collectively produce a desired therapeutic benefit.

The systems and methods of the present invention are particularly suited for determining the pharmacokinetics and metabolism associated with such unregulated group of composition and extracts to thus enable the same to be manufactured and formulated pursuant to standardized dosages. The systems and methods of the present invention are further particularly well-suited for developing extracts of such unregulated herbal remedy/plant extract compositions for use in deriving orally-administered formulations, such as tablets, liquid suspensions, and the like, to be administered on a periodic (i.e., daily) basis.

As is well-known, all orally administered pharmaceutical compositions are designed to be absorbed at one or more specific sites along the gastrointestinal tract. In human beings, the gastrointestinal tract comprises, in sequential order, the mouth, esophagus, stomach, small intestine including the duodenum, jejunum, ileum and cecum, and large intestine. As a given pharmaceutical composition sequentially passes through the gastrointestinal tract, such composition is subjected to enzymatic attack from a variety of digestive enzymes, as well as significant fluctuations in pH. For example, gastric juices have a pH of approximately 1.6 and contain numerous proteolytic enzymes, such as pepsin. The contents from the stomach, however, when passed to the duodenum of the small intestine, are caused to experience a rapid rise in pH from 7 to 8, and are further contacted with digestive enzymes furnished by the pancreas and epithelium of the small intestine.

Although such digestion begins in the stomach, however, it is well-known that the final stages of digestion and absorption of most chemical compounds, including all major food components into the blood take place in the small intestine. The cross-section of intestinal tissue depicted in FIG. 1 illustrates the intestinal villi 12 formed within the lumen of the small intestine which come into with the gastric contents. Such villi 12 provide a very large surface area through which such products can be rapidly transported through the epithelial cells and into the blood capillaries and lymph vessels inside. Beneath the layer of intestinal villi 12 is the lamina propria 14 followed by the muscularis mucosa 16 which collectively cooperate to define the mucosa 18 of the small intestine. Lying thereunderneath is the submucosa 20 and muscularis 22, the latter being comprised of muscular tissue, namely the stratum circularis 24 and stratum longitudinalis 26 with the outer serosa layer 28 covering the outermost portion thereof. As is well-understood, the mucosa, submucosa, and muscularis, as well as the subparts thereof, cooperate to define the tissue through which orally-ingested compositions are typically absorbed from the gastrointestinal tract and systemically distributed throughout the body.

For use in the absorption system and method of the present invention, a cross-section of such intestinal tissue, which may be harvested from any suitable mammalian model, such as a rabbit or rat, is obtained to analyze, in vitro, the rate or rates of absorption a given pharmaceutical composition attains across such tissue over a given period of time, discussed more fully below. With respect to the section of intestinal tissue obtained, it is believed that intestinal tissue obtained from rabbits or cats is most suited for analyzing the absorption rate that most closely approximates those experienced in the human body. Such section of tissue may be harvested by any of well-known clinical procedures currently in use provided, however, the biological activity of such tissue is preserved as much as possible utilizing conventional tissue-preserving techniques. In this regard, it is contemplated that such harvested tissue should be utilized in the practice of the present invention as quickly as possible to more closely mimic the rates of absorption that would occur in vivo. Specifically, it is believed that to the extent such harvested tissue is not utilized within one to two hours of being harvested for use in the present invention, such section of tissue should not be utilized. It is contemplated, however, that such tissue may be preserved in a suitable buffer solution with one or more suitable preservatives for a duration up to four hours and still be suitable for use in the practice of the present invention.

To date, it is believed that it is necessary to obtain a section of intestinal tissue having a surface area no smaller than approximately 1.78 square centimeters in order to provide enough area to adequately assess absorption rates, although it is contemplated that smaller or larger sections of tissue may possibly be utilized in the practice of the present invention. In any application, however, it is essential that the section of tissue so harvested not be perforated at any point thereabout or otherwise be degraded such that the various layers comprising the section of tissue are sufficiently damaged so as to not possess the thickness or structural integrity resembling live or freshly harvested tissue.

Figure 2:
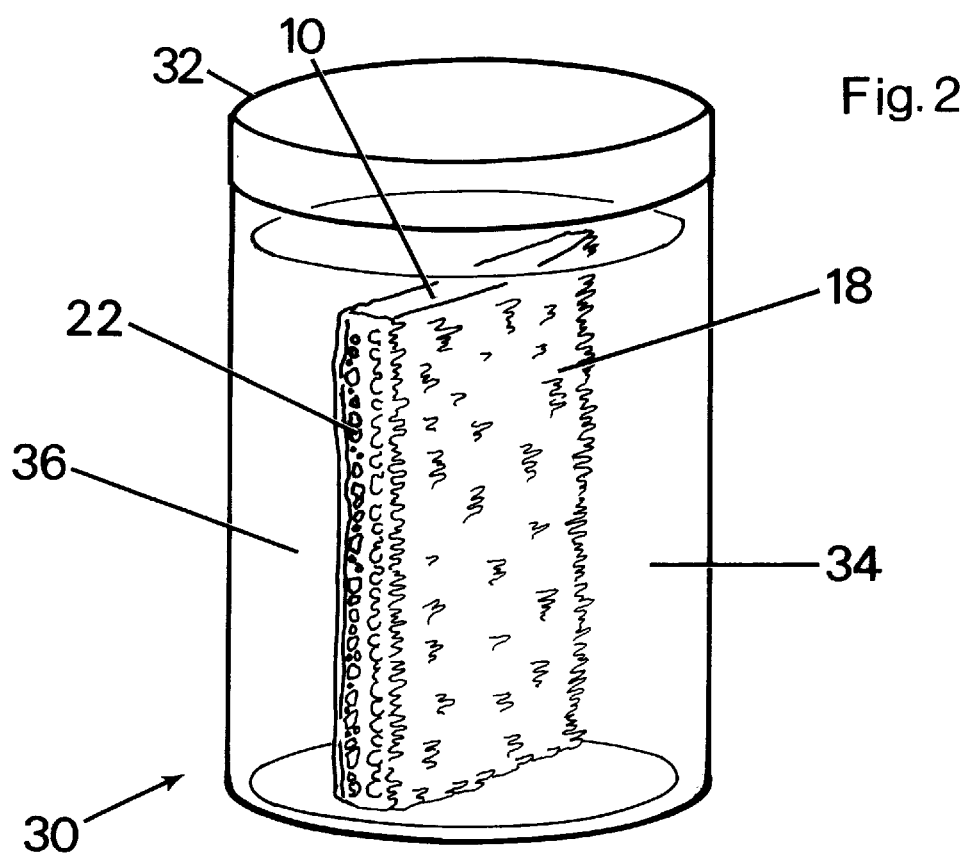
FIG. 2 is cross-sectional view of a system for determining the rate of absorption of a pharmaceutical composition, as well as any sub-components or metabolites thereof, through a section of ileal wall as constructed in accordance with a preferred embodiment of the present invention.

Once properly obtained, the section of intestine 10 is mounted as a filter into a suitable chamber mechanism 32, which preferably comprises an Ussing chamber, as depicted in FIG. 2. The Ussing chamber 32 is profused by a biologically compatible buffer, such as a phosphate buffer or tris buffer, having a pH ranging from between 7 to 8. The section of intestinal tissue 10 is so positioned within the chamber 32 such that there are defined two sub-chambers, namely, a first sub-chamber 34 defined by approximately one-half of the chamber 32 and the mucosal side 18 of the tissue 10, including the intestinal villi 12, and a second sub-chamber 36 defined by the remaining portion of the chamber 32 and the muscularis 22 of the intestinal tissue 10, as defined by the serosa 28. Within the first chamber 34, there is added a known concentration of the pharmaceutical composition, the absorption rate of which is sought to be determined. In this regard, it is contemplated that the concentration of such composition will have been determined beforehand with such composition being introduced into such first chamber 34 as an aqueous solution with the pharmaceutical composition being suspended or dissolved therein. As will be appreciated by those skilled in the art, the concentration of any such compound tested via the systems and methods of the present invention should preferably be saturated in DMSO (i.e., dimethyl sulphoxide) and subsequently diluted to a solution containing 1% DMSO concentration.

In a more highly preferred embodiment of the present invention, it is contemplated that the pharmaceutical composition, as suspended within the aqueous solution introduced into the first chamber 34, will have previously been subjected to gastric juices to thus mimic the effect such juices would have upon the pharmaceutical composition prior to when such composition ultimately comes into contact with the small intestine, as would occur when such pharmaceutical compositions would be ingested in the human gastrointestinal tract. In this respect, the low pH of gastric juices, coupled with the proteolytic enzymes present therein, are known to diminish the biologically active components of some herbal remedies and plant extracts, as well as affect their ability to be absorbed at points later on in the gastrointestinal tract.

Prior to or simultaneously with the introduction of the aqueous suspension or solution of the pharmaceutical composition introduced in the first chamber 34, there is placed in the second chamber 36 an appropriate amount of liquid plasma or buffer solution containing an appropriate level of plasma protein dissolved or suspended therein within the second chamber. As will be appreciated by those skilled in the art, the second chamber 36 is designed to reproduce the host's blood plasma serum, which serves as a measure of the degree and extent the pharmaceutical composition is systemically absorbed for purposes of analyzing the specific pharmacokinetics associated with such composition, and in particular, peak plasma concentrations.

Once so arranged in the aforementioned manner, the flux of the pharmaceutical composition, as well as any sub-components or metabolites thereof, through the section of intestine, as indicated by the letter A, is measured by analyzing the concentration of such composition, sub-components and/or metabolites in the second chamber 36 at periodic intervals. In this regard, such concentrations may be determined by any of a variety of qualitative and quantitative techniques known in the art, such as liquid and/or gas chromatography and/or mass spectrometry. Additionally, it is contemplated that such absorption rates may be determined by measuring the extent of protein binding such composition (or metabolites) achieves with the serum protein suspended in the second chamber 36, which is thus indicative of systemic bioavailability. Along these lines, it is contemplated that the system and methods of the present invention may be useful in not only determining the rate of absorption and serum concentration levels achieved by a given pharmaceutical composition at a given concentration, but may be further useful in identifying those components or metabolites thereof that are responsible for generating the therapeutic effects, and thus provides means for identifying the active ingredients associated with such components.

As will be appreciated by those skilled in the art, the absorption system and method of the present invention, by virtue of their ability to identify the various components and/or metabolites of a given herbal remedy or plant extract, as well as their respective concentrations, permit such data to be utilized to create standardized herbal extracts. As has not heretofore been available, the systems and methods of the present invention serve the dual purpose of not only identifying certain target compounds or markers that, either alone or collectively, produce the desired benefit, but also the respective concentrations the same can achieve in the bloodstream via the gastrointestinal tract. The systems and methods of the present invention are particularly effective in identifying multi-component herbal remedies and plant extracts that utilize a plurality of components and/or metabolites in varying concentrations to collectively produce a desired therapeutic benefit. In this regard, the systems and methods of the present invention enable each respective compound to be identified as a specific marker that must necessarily be present at a specified concentration. Identification of such specific markers may thus be utilized to guide and regulate the extraction process, thereby creating potentially more effective extracts. As has been a long-recognized problem in the art, the choice of components or markers of multi-component herbal remedies and plant extracts is arbitrary, and currently no standardized procedure exists for formulating the same, let alone systems and methods for deriving extracts based upon absorption potential coupled to pharmacological properties.

In addition to utilizing intestinal tissue, which may be selected from either the duodenum, jejunum, ileum or cecum, it is further contemplated that other tissues or cell lines through which pharmaceutical compositions may be absorbed may be utilized in the practice of the present invention. For example, it is contemplated that a section of stomach wall or colonic wall may be utilized to determine absorption rates through those respective tissues as per the above methodology. It will be understood, however, that to closely mimic the in vivo environment, adjustments must be made with respect to such factors as pH and/or the aerobic or anaerobic conditions inherent to such tissue to thus approximate the conditions under which absorption would take place as if in a living organism.

Although the invention has been described herein with specific reference to a presently preferred embodiment thereof, it will be appreciated by those skilled in the art that various modifications, deletions, and alterations may be made to such preferred embodiment without departing from the spirit and scope of the invention. Accordingly, it is intended that all reasonably foreseeable additions, modifications, deletions and alterations be included within the scope of the invention as defined in the following claims.

What is claimed is:

1. A system for detecting in vitro the pharmaceutically active ingredient of a pharmaceutical composition as absorbed from the gastrointestinal tract of a mammal comprising:

a) a cross-section of gastrointestinal tissue harvested from a mammal selected from the group consisting of rats and rabbits, said section of tissue being so harvested such that said tissue retains a first side defined by the mucosa of such tissue and a second side defined by the muscularis of such tissue;

b) a chamber for receiving and retaining said harvested tissue therein, said chamber being designed to retain said tissue such that said chamber and tissue cooperate to define first and second sub-chambers, said first chamber being defined by a portion of said container and said first side of said tissue, and said second chamber being defined by a portion of said chamber and said second side of said tissue;

c) a first solution having a known concentration of said pharmaceutical composition dissolved therein, said solution being contacted with and stored within said first sub-chamber;

d) a second solution comprising a biologically compatible buffer, said second solution being contacted with and stored within said second sub-chamber; and e) a chemical analysis mechanism for periodically sampling said second solution and detecting the presence of said pharmaceutically active ingredient of said, pharmaceutical composition therein such that when said first solution is contained within said first sub-chamber, the rate of diffusion by which said pharmaceutically active ingredient of said pharmaceutical composition diffuses across said section of gastrointestinal tissue can be measured at periodic intervals.

2. The system of claim 1 wherein said section of gastrointestinal tissue comprises tissue harvested from the esophagus, stomach, small intestine and colon of said mammal.

3. The system of claim 2 wherein when said tissue is harvested from said small intestine, said tissue is harvested from a site along the small intestine consisting of the duodenum, jejunum, ileum and cecum.

4. The system of claim 2 wherein when said tissue comprises stomach tissue, said first solution has a pH ranging from about 1.0 to 2.0.

5. The system of claim 1 wherein said first and second solutions have a pH ranging from approximately 7 to 8.

6. The system of claim 1 wherein said second solution comprises liquid plasma.

7. The system of claim 1 wherein said pharmaceutical composition comprises an herbal remedy.

8. The system of claim 7 wherein said chemical analysis mechanism detects the presence of at least one component of said herbal remedy such that when said first solution is contained with said first sub-chamber, the rate of diffusion by which said at least one component of said herbal remedy diffuses across said section of gastrointestinal tissue can be measured at periodic intervals.

9. The system of claim 8 wherein said chemical analysis mechanism detects the presence of a plurality of components of said herbal remedy such that when said first solution is contained with said first sub-chamber, the rate of diffusion by which each respective one of said plurality of components of said herbal remedy diffuses across said section of gastrointestinal tissue can be measured at periodic intervals.

10. The system of claim 1 wherein said pharmaceutical composition comprises a plant extract.

11. The system of claim 10 wherein said chemical analysis mechanism detects the presence of at least one component of said plant extract such that when said first solution is contained with said first sub-chamber, the rate of diffusion by which said at least one component of said plant extract diffuses across said section of gastrointestinal tissue can be measured at periodic intervals.

12. The system of claim 10 wherein said chemical analysis mechanism detects the presence of a plurality of components of said plant extract such that when said first solution is contained with said first sub-chamber, the rate of diffusion by which each respective one of said plurality of components of said plant extract diffuses across said section of gastrointestinal tissue can be measured at periodic intervals.

13. A method for detecting in vitro the pharmaceutically active ingredient of a pharmaceutical composition as absorbed from the gastrointestinal tract of a mammal comprising:

a) providing a cross-section of gastrointestinal tissue harvested from a mammal selected from the group consisting of rats and rabbits, said section of tissue being so harvested such that said tissue includes a first side defined by the mucosa of such tissue and a second side defined by the muscularis of such tissue; a chamber for receiving and retaining said section of tissue therein, a first solution having a known concentration of said pharmaceutical composition dissolved therein, a second solution comprising a biologically compatible buffer;

b) securing said tissue within said chamber such that said tissue and chamber cooperate to define first and second sub-chambers, said first chamber being defined by a portion of said container and said first side of said tissue, and said second chamber being defined by a portion of said chamber and said second side of said tissue;

c) contacting said first chamber with said first solution;

d) contacting said second chamber with said second solution; and e) periodically analyzing said second solution to determine the presence of said pharmaceutically active ingredient of said pharmaceutical composition absorbed from said first solution through said harvested tissue.

14. The method of claim 13 wherein in step a), said gastrointestinal tissue is harvested from said mammal at a site selected from the group consisting of the esophagus, stomach, small intestine, and large intestine.

15. The method of claim 13 wherein when said tissue is harvested from said small intestine, said tissue is harvested from a site along the small intestine consisting of the duodenum, jejunum, ileum and cecum.

16. The method of claim 13 wherein prior to step c), said first solution is contacted with gastric juice for a duration sufficient to allow said gastric juice to thoroughly become contacted with said pharmaceutical composition.

17. The method of claim 13 wherein said pharmaceutical composition is an herbal remedy.

18. The method of claim 13 wherein said chemical analysis mechanism detects the presence of at least one component of said herbal remedy such that said second solution is periodically analyzed to determine the presence of said at least one component of said herbal remedy absorbed from said first solution through said harvested tissue.

19. The method of claim 13 wherein said chemical analysis mechanism detects the presence of a plurality of components of said herbal remedy such that said second solution is periodically analyzed to determine the presence of each respective one of said plurality of components of said herbal remedy absorbed from said first solution through said harvested tissue.

20. The method of claim 13 wherein said pharmaceutical composition is a plant extract.

21. The method of claim 13 wherein said chemical analysis mechanism detects the presence of at least one component of said plant extract such that said second solution is periodically analyzed to determine the presence of said at least one component of said plant extract absorbed from said first solution through said harvested tissue.

22. The method of claim 13 wherein said chemical analysis mechanism detects the presence of a plurality of components of said plant extract such that said second solution is periodically analyzed to determine the presence of each respective one of said plurality of components of said plant extract absorbed from said first solution through said harvested tissue.

23. The method of claim 13 wherein in step e), said testing of said second solution is conducted at intervals from 30 to 60 minutes for up to 4 hours.

24. The method of claim 13 wherein in step e), said chemical analysis is performed by liquid chromatography.

25. The method of claim 13 wherein in step e), said chemical analysis is performed by gas chromatography.

26. The method of claim 13 wherein in step e), said chemical analysis is performed by mass spectrometry.

27. The method of claim 13 wherein said solution comprises liquid plasma and in step e), said chemical analysis comprises determining the amount of pharmaceutical composition bound to the proteins suspended within said plasma.

28. The method of claim 13 wherein said solution comprises blood plasma and in step e), said chemical analysis comprises determining the amount of pharmaceutical composition bound to the proteins suspended within said plasma.

* * * * *